United States Patent
Tamada (10) Patent No.: US 8,873,039 B2
(45) Date of Patent: Oct. 28, 2014

(54) NON-LINEAR RAMAN SPECTROSCOPY APPARATUS, NON-LINEAR SYSTEM, AND NON-LINEAR RAMAN SPECTROSCOPY METHOD

(75) Inventor: Sakuya Tamada, Tokyo (JP)

(73) Assignee: Sony Corporation, Tokyo (JP)

( * ) Notice: Subject to any disclaimer, the term of this patent is extended or adjusted under 35 U.S.C. 154(b) by 302 days.

(21) Appl. No.: 13/407,447

(22) Filed: Feb. 28, 2012

(65) Prior Publication Data
US 2012/0250013 A1 Oct. 4, 2012

(30) Foreign Application Priority Data
Mar. 31, 2011 (JP) ................................. 2011-079473

(51) Int. Cl.
*G01J 3/44* (2006.01)
*G01N 21/65* (2006.01)
(52) U.S. Cl.
CPC ..................................... *G01N 21/65* (2013.01)
USPC ........................................................ 356/301

(58) Field of Classification Search
USPC .............................................. 356/301, 72–73
See application file for complete search history.

(56) References Cited

U.S. PATENT DOCUMENTS

2007/0088219 A1* 4/2007 Xie et al. ...................... 600/473

FOREIGN PATENT DOCUMENTS

| JP | 05-288681 | 11/1993 |
| JP | 2004-061411 | 2/2004 |
| JP | 2006-276667 | 10/2006 |
| JP | 2009-222531 | 10/2009 |
| JP | 2010-002256 | 1/2010 |

\* cited by examiner

*Primary Examiner* — Abdullahi Nur
(74) *Attorney, Agent, or Firm* — K&L Gates LLP (57) ABSTRACT

A non-linear Raman spectroscopy apparatus includes a light source unit emitting a pulse beam having a pulse width of 0.2 ns to 10 ns, a pulse peak power of 50 W to 5000 W, and a wavelength of 500 nm to 1200 nm, and a single-mode fiber through which continuous white light is generated from the pulse beam. A test sample to be measured is radiated with a pump-cum-probe beam formed of the pulse beam and a Stokes beam formed of the continuous white light to obtain a Raman spectrum.

11 Claims, 10 Drawing Sheets

NON-LINEAR RAMAN SPECTROSCOPY APPARATUS, NON-LINEAR SYSTEM, AND NON-LINEAR RAMAN SPECTROSCOPY METHOD

CROSS REFERENCES TO RELATED APPLICATIONS

The present application claims priority to Japanese Priority Patent Application JP 2011-079473 filed in the Japan Patent Office on Mar. 31, 2011, the entire content of which is hereby incorporated by reference.

BACKGROUND

The present disclosure relates to a non-linear Raman spectroscopy apparatus, and a non-linear Raman spectroscopy system and non-linear Raman spectroscopy method that use this apparatus. In more detail, the present disclosure relates to an apparatus, system, and method for multiplex coherent anti-Stokes Raman spectroscopy using a broadband light source as a Stokes beam.

Laser Raman spectroscopy is an analysis method of radiating a test sample with laser light having a single wavelength as a pump beam and obtaining spectrums of light scattered from the test sample. A shift amount of the wave number of a Stokes beam or an anti-Stokes beam, which is the scattered light mentioned above, with respect to the wave number of a pump beam is observed as a substance-specific spectrum, which corresponds to a molecular vibration mode unique to the substance of the test sample. Therefore, together with infrared spectroscopy, Raman spectroscopy has been widely used as spectroscopy for a molecular fingerprint region to analyze and evaluate substances, perform medical diagnoses, and develop organics such as new drugs and foods.

Non-linear Raman spectroscopy is similar to the laser Raman spectroscopy in the past described above in that Raman scattering light is measured, but is different therefrom in that a third-order non-linear optical process is used. The third-order non-linear optical process is to detect scattering light in three types of incident light as excitation beams, that is, a pump beam, a probe beam, and a Stokes beam. Examples include CARS (coherent anti-Stokes Raman scattering), CSRS (coherent Stokes Raman scattering), stimulated Raman loss spectroscopy, and stimulated Raman gain spectroscopy.

In CARS spectroscopy, in general, a test sample is radiated with a pump beam and a Stokes beam having a wavelength longer than that of the pump beam, and spectrums are obtained from non-linear Raman scattering light having a wavelength shorter than that of the pump beam scattered from the test sample (for example, refer to Japanese Unexamined Patent Application Publication No. 5-288681, Japanese Unexamined Patent Application Publication No. 2006-276667, and Japanese Unexamined Patent Application Publication No. 2010-2256). Also, a non-linear Raman spectroscopy method using white light as a light source for generating a Stokes beam has been suggested in the past (refer to Japanese Unexamined Patent Application Publication No. 2004-61411 (Japanese Patent No. 3691813)).

On the other hand, in CARS spectroscopy in the past described above, ultrashort pulse light of several tens of fs to several tens of ps is used as laser light for generating a pump beam and a Stokes beam. In this case, there is a problem such that an apparatus for use in CARS is expensive and complex. To avoid this problem, a method of using a supercontinuum light excited by a short pulse having a pulse width of 0.1 ns to 10 ns with a photonic crystal fiber (PCF) has been suggested (refer to Japanese Unexamined Patent Application Publication No. 2009-222531).

Compared with Raman spectroscopy in the past, non-linear Raman spectroscopy typified by CARS spectroscopy described above can avoid an influence of fluorescence background, and further improve detection sensitivity. For this reason, non-linear Raman spectroscopy has been actively studied and developed particularly as a molecular imaging technology of biosystems.

SUMMARY

However, in the non-linear Raman spectroscopy in the past described above, particularly multiplex CARS spectroscopy, broadband white light is generated with a PCF, a highly non-linear fiber (HNLF), or the like, thereby causing a large optical damage particularly near an incident end face to limit a maximum incident power.

In general, when a PCF or an HNLF is used, there is an advantage that a wideness of its spectrum can be ensured. In CARS spectroscopy, however, the excess wideness results in decrease of optical power density per unit wavelength.

Also, the PCF has a problem such that a special end-face processing is to be performed.

Moreover, a beam profile of supercontinuum light (beam) generated from a PCF is generally not that of an ideal Gaussian beam. Laser light having this beam profile is not preferable because this may cause degradation of an image obtained by microspectroscopy or microspectroscopic imaging.

Thus, it is desirable to mainly provide a highly-efficient, excellently-stable, and small-sized non-linear Raman spectroscopy apparatus, non-linear Raman spectroscopy system, and non-linear Raman spectroscopy method.

To address the problems described above, as a result of diligent experiments and studies, the inventor has gained the following findings. In particular, for application to biosystems, obtaining spectrums in a molecular vibration spectrum region called a molecular fingerprint region of 300 cm$^{-1}$ to 3600 cm$^{-1}$ is important. For this reason in microspectroscopic imaging by a non-linear Raman spectroscopy, to improve a non-linear optical effect representing quality of an input laser beam, a high peak power, a Gaussian beam, and a linear polarization state are desired.

On the other hand, a spatial intensity distribution of light emitted from a single-mode fiber (SMF) is of an ideal Gaussian beam if the wavelength of emitted light is near or longer than a cut-off wavelength of the SMF. Thus, the inventor has studied the use of an SMF, which is inexpensive and easily available, in place of a PCF or a HNLF, for generating broadband white light for a Stokes beam. As a result, the inventor has found that an ideal Gaussian beam can be obtained also by using an SMF.

Furthermore, in non-linear Raman spectroscopy, polarization plane (directions of electric field vectors) of three pulses of a pump beam, a probe beam, and a Stokes beam desirably match with each other. Regarding this point, the inventor has found that an excellent linearly-polarized Stokes beam can be obtained by using a specific SMF, in particular, a polarization-maintained single-mode fiber (PF-SMF), thereby reaching embodiments of the present disclosure.

That is, a non-linear Raman spectroscopy apparatus according to an embodiment of the present disclosure includes a light source unit emitting a pulse beam having a pulse width of 0.2 ns to 10 ns, a pulse peak power of 50 W to 5000 W, and a wavelength of 500 nm to 1200 nm and a single-mode fiber through which continuous white light is generated from the pulse beam, and a test sample to be measured is radiated with a pump-cum-probe beam formed of the pulse beam and a Stokes beam formed of the continuous white light to obtain a Raman spectrum.

In this apparatus, for example, a polarization-maintained single-mode fiber can be used as the single-mode fiber.

In this case, a half-wave plate rotating a plane of polarization of the pulse beam introduced from the light source unit may be provided, and the pulse beam having the plane of polarization rotated by the half-wave plate so as to be parallel to a fast axis or a slow axis of the single-mode fiber may enter the single-mode fiber.

Also, a half-wave plate matching a direction of a plane of polarization of the pump-cum-probe beam with a plane of polarization of the Stokes beam can be provided.

On the other hand, the single-mode fiber can have a fiber length of, for example, 1 m to 20 m.

Furthermore, an optical fiber may further be provided through which an optical path length of the pump-cum-probe beam is adjusted so that the test sample is radiated with the pump-cum-probe beam and the Stokes beam simultaneously.

In this case, as the optical fiber, a single-mode fiber or a polarization-maintained single-mode fiber can be used when a low excitation power equal to or lower than several mW is inputted through the optical fiber. When an excitation power equal to or larger than several mW is inputted, the fiber core diameter is increased as appropriate and a polarization-maintained single-mode fiber having a fiber core diameter equal to or larger than 8 μm, a multimode fiber having a core diameter equal to or smaller than 100 μm, a large-mode-area fiber, or a photonic crystal large-mode-area fiber can be used.

A non-linear Raman spectroscopy system according to another embodiment of the present disclosure includes the non-linear Raman spectroscopy apparatus described above and a computing device normalizing a Raman spectroscopic spectrum measured in the non-linear Raman spectroscopy apparatus.

In this system, in the computing device, when $\omega$ and $\omega'$ each represent a wave number (cm$^{-1}$), a normalization factor $R_N(\omega)$ can be calculated from a power $P_P$ of the pump beam and an intensity spectrum distribution $S_S(\omega)$ of the Stokes beam based on Expression 1 below, and a measurement spectrum $S_C(\omega)$ can be normalized with the normalization factor $R_N(\omega)$ based on Expression 2 below to find a normalized spectrum $S_N(\omega)$.

$$R_N(\omega) = \left(\frac{P_P}{2}\right)^2 S_S(\omega) + P_P \int S_S(\omega') S_S(\omega + \omega') d\omega' \quad \text{Expression 1}$$

$$S_N(\omega) = \frac{S_C(\omega)}{R_N(\omega)} \quad \text{Expression 2}$$

In this case, in the non-linear Raman spectroscopy apparatus, a long-pass filter or a band-pass filter having an edge wavelength $\lambda_e$ (nm) on a short-wavelength side in a range represented by Expression 3 below may be provided on an emission side of the single-mode fiber. Note that in Expression 3 below, $\lambda_p$ is a wavelength (nm) of the pump beam, and $\lambda_f$ is a value found from Expression 4 below. Also, in Expression 4, $\omega_m$ is a measurement maximum wave number (cm$^{-1}$).

$$\lambda_p \leq \lambda_e \leq \frac{2\lambda_p \lambda_f}{\lambda_p + \lambda_f} \quad \text{Expression 3}$$

$$\lambda_f = \frac{1 \times 10^7 \cdot \lambda_p}{1 \times 10^7 - \omega_m \cdot \lambda_p} \quad \text{Expression 4}$$

A non-linear Raman spectroscopy method according to still another embodiment of the present disclosure includes emitting a pulse beam from a light source unit, the pulse beam having a pulse width of 0.2 ns to 10 ns, a pulse peak power of 50 W to 5000 W, and a wavelength of 500 nm to 1200 nm, generating continuous white light from the pulse beam through a single-mode fiber, and radiating a test sample to be measured with a pump-cum-probe beam formed of the pulse beam and a Stokes beam formed of the continuous white light to obtain a Raman spectrum.

According to the embodiments of the present disclosure, a Stokes beam formed of continuous white light is generated with a single-mode fiber. Therefore, a highly-efficient, excellently-stable, and small-sized non-linear Raman spectroscopy apparatus and non-linear Raman spectroscopy method can be provided.

Additional features and advantages are described herein, and will be apparent from the following Detailed Description and the figures.

DETAILED DESCRIPTION

Figure 1:
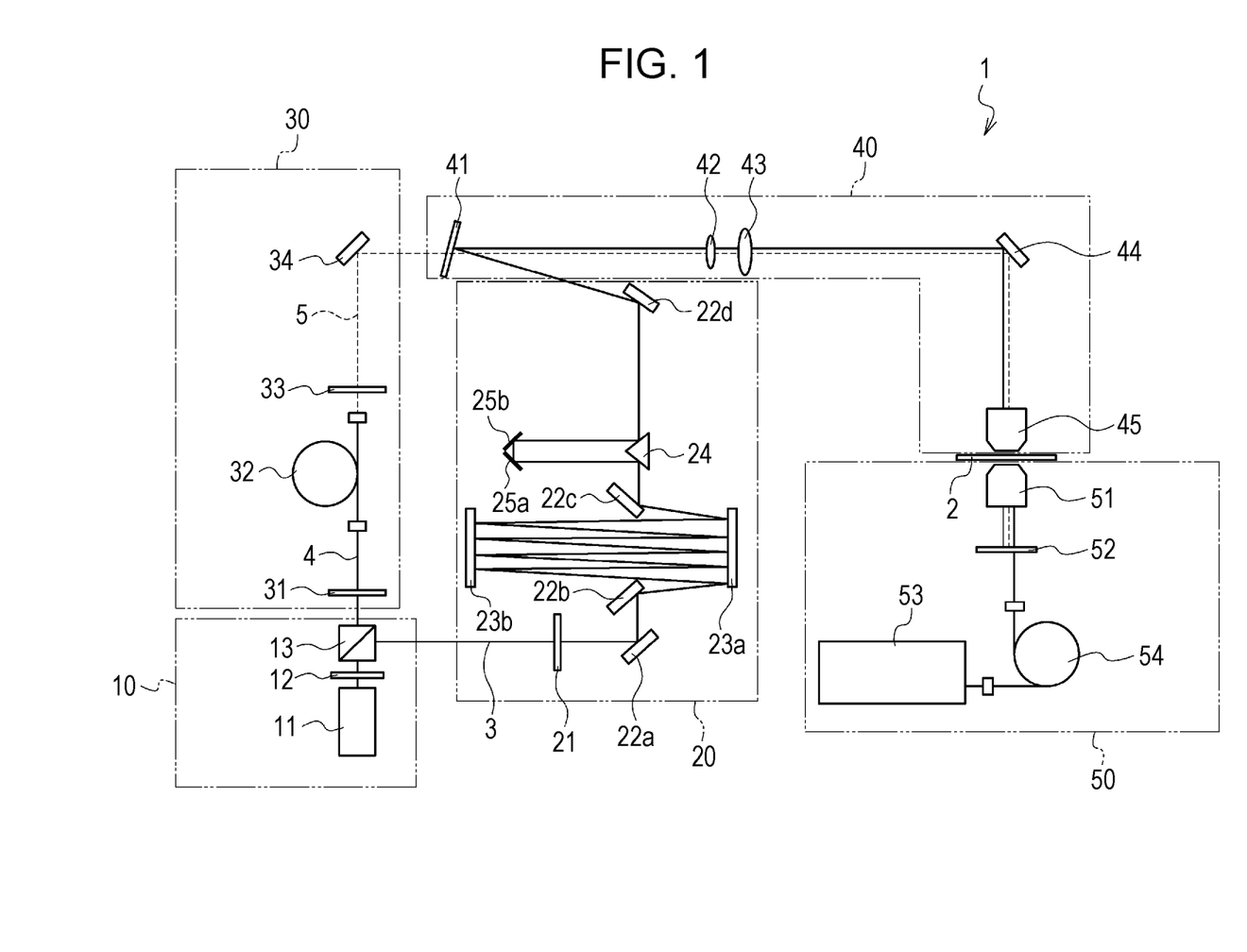
FIG. 1 is a schematic diagram of the structure of a non-linear Raman spectroscopy apparatus according to an embodiment of the present disclosure.

Embodiments of the present disclosure are described in detail below with reference to the attached drawings. Note that the present disclosure is not meant to be restricted to each of the embodiments shown below. The description is made in the following sequence.
1. Embodiment
(Example of an apparatus using a single-mode fiber for generation of a Stokes beam)
2. Another Embodiment
(Example of an apparatus in which an optical fiber is placed on an optical path of a pump-cum-probe beam)
3. Still Another Embodiment
(Example of a system including a computing unit normalizing a measured spectrum) 1. Embodiment
Entire Structure of the Apparatus First, a non-linear Raman spectroscopy apparatus according to an embodiment of the present disclosure is described. FIG. 1 is a schematic diagram of the structure of a non-linear Raman spectroscopy apparatus of the present embodiment. A non-linear Raman spectroscopy apparatus 1 of the present embodiment is a CARS spectroscopy apparatus and, as shown in FIG. 1, is provided with a light source unit 10, a pump-cum-probe-beam generating unit 20, a Stokes-beam generating unit 30, a beam radiating unit 40, and a measuring unit 50.
Light Source Unit 10

The light source unit 10 includes at least a laser 11 emitting a pulse beam and a polarization beam splitter 13 distributing the pulse beam to the pump-cum-probe-beam generating unit 20 and the Stokes-beam generating unit 30. The light source unit 10 emits a predetermined pulse beam toward the pump-cum-probe-beam generating unit 20 and the Stokes-beam generating unit 30.

Here, the laser 11 can be any as long as it can generate a pulse beam having a pulse width of 0.2 ns to 10 ns, a pulse peak power of 50 W to 5 kW, and a wavelength of 500 nm to 1200 nm. For example, an inexpensive, small-sized Nd:YAG laser generating sub-nano-second repeated pulses of a Q switch type oscillating at 1064 nm can be used. Other than the Q switch type, an Nd:YAG, Nd:YVO$_4$, or Nd:YLF picosecond laser and a Yb-base-doped-fiber pico-second laser of a mode lock type can also be used, for example.

Furthermore, when a beam having a short wavelength is used for measurement, with a beam from each laser described above as an excitation beam, a second harmonic generation (SHG) optical crystal, such as KTP or LBO, may be used to generate an SHG beam. In this case, when the wavelength of the excitation beam is 1064 nm, the wavelength after wavelength conversion due to second harmonic generation is 532 nm. As such, in the non-linear Raman spectroscopy apparatus 1 of the present embodiment, a component emitting a beam having a wavelength of 532 nm or 1064 nm can be suitably used.

Note that the wavelength of the pulse beam emitted from the light source unit 10 is not meant to be restricted to these. For example, in the case of the Nd:YAG laser, a beam having a wavelength of 1319 nm, 1122 nm, or 946 nm in addition to 1064 nm can be oscillated. Also, in the case of the Nd:YVO$_4$ laser, a beam having a wavelength of 1342 nm or 914 nm in addition to 1064 nm can be oscillated. Furthermore, in the case of the Nd:YLF laser, a beam having a wavelength of 1053 nm or 1047 nm can be oscillated. In the case of the Yb:YAG laser, a beam having a wavelength of 1030 nm can be oscillated.

When a second harmonic is generated with these wavelengths as fundamental waves, SHG beams having wavelengths of 660 nm, 561 nm, 473 nm, 671 nm, 457 nm, 527 nm, 523 nm, and 515 nm in addition to 532 nm can be obtained.

However, if the pulse width is shorter than 0.2 ns, the laser mechanism is complex and expensive. On the other hand, if the pulse width exceeds 10 nm, pulse energy per one shot is too large. Specifically, the pulse energy of the laser beam is equal to or larger than 5 µJ, possibly causing a damage on the end face of the optical fiber and making the performance of the Stokes beam unstable. Also, as a matter of course, power consumption at the time of laser operation is increased. Note that the pulse width of a pulse beam emitted from the laser 11 is preferably 0.4 ns to 5 ns.

In order to obtain a third-order non-linear optical effect for obtaining continuous white light in an optical fiber having a short length, the peak power of the pulse beam is preferably high. Thus, in the non-linear Raman spectroscopy apparatus 1 of the present embodiment, in order to increase the pulse energy, the peak power is increased, but the pulse width is decreased accordingly, thereby decreasing the pulse energy per shot to prevent average power from increasing in accordance with a repetition rate. For example, if the pulse width is within the range described above and the repetition rate is 10 kHz to 50 kHz, the average power is set to be equal to or lower than 250 mW.

As the light source unit 10 satisfying the specifications as described above, for example, the structure can be thought in which an Nd:YAG solid laser of a passive Q switch type (PLUSELAS P-1064-300 manufactured by ALPHALAS GmbH) is equipped with a second-harmonic-generation KTP crystal SHG unit. In this structure, for example, a beam having a wavelength of 532 nm, an average power of 100 mW, a pulse width of 600 ps, and a repetition rate of 30 kHz can be emitted.

Also, in the light source unit 10, a half-wave plate 12 may be placed between the laser 11 and the polarization beam splitter 13. The half-wave plate 12 is a polarization element rotating the plane of polarization of a beam emitted from the laser 11. When the optical axis of the half-wave plate 12 is rotated by θ, the plane of polarization of the laser beam after passage is rotated by 2θ. With this, the beam emitted from the laser 11 is distributed into vertical polarization and horizontal polarization. Therefore, distribution can be suitably made into an excitation pulse beam 4 and a pump-cum-probe beam (hereinafter simply referred to as a pump beam) 3 in the polarization beam splitter 13.
Pump-Cum-Probe-Beam Generating Unit 20

The pump-cum-probe-beam generating unit 20 is provided with an optical-path-length adjusting mechanism in order to apply the pulse beam (the pump beam 3) entering from the light source unit 10 together with a Stokes beam 5, which will be described further below. Specifically, the optical path length of the pump beam 3 is adjusted by reflecting the pump beam 3 off a plurality of mirrors 22a to 22d, 23a, 23b, 24, 25a, and 25b, thereby matching with the Stokes beam 5 in timing.

Note that the optical-path-length adjusting mechanism is not meant to be restricted to the structure shown in FIG. 1. For example, if the optical path length of the pump beam 3 can be matched with the optical path length of the Stokes beam 5 with optical arrangement of the mirrors 22a to 22d, 23a, and 23b, the mirrors 24, 25a, and 25b can be eliminated.

Also, when a polarization-maintained single-mode fiber, which will be described further below, is used as the single-mode fiber 32, a half-wave plate 21 is placed before the first mirror 22a to match the direction of the plane of polarization of the pump beam 3 with the direction of the plane of polarization of the Stokes beam 5. Note that when a normal single-mode fiber is used, the half-wave plate 21 can be eliminated.

Stokes-Beam Generating Unit 30

The Stokes-beam generating unit 30 generates the Stokes beam 5, which is continuous white light, from the pulse beam 4 entering from the light source unit 10, and includes at least the single-mode fiber 32. Here, the wave range of the Stokes beam 5 is that of a Stokes beam corresponding to a molecular fingerprint region (300 cm$^{-1}$ to 3600 cm$^{-1}$ in Raman shift amount), and is represented by Expression 5 below. Note that λ in Expression 5 below represents a wavelength (nm) of a Stokes beam, $\lambda_p$ represents a wavelength (nm) of a pump beam, and a relation between the wave number ω (cm$^{-1}$) and the wavelength λ (nm) can be represented by Expression 6 below.

$$\frac{1 \times 10^7}{\frac{1 \times 10^7}{\lambda_p} - 300} \leq \lambda \leq \frac{1 \times 10^7}{\frac{1 \times 10^7}{\lambda_p} - 3600} \qquad \text{Expression 5}$$

$$\omega \cdot \lambda = 1 \times 10^7 \qquad \text{Expression 6}$$

The wavelength λ of the Stokes beam 5 generated in the Stokes-beam generating unit 30 is 540 nm to 660 nm when a wavelength $\lambda_p$ of the pump beam 3 is 532 nm, and is 1100 nm to 1725 nm when the wavelength $\lambda_p$ of the pump beam 3 is 1064 nm.

The single-mode fiber 32 provided in the Stokes-beam generating unit 30 can be any as long as it has a fiber length of 1 m to 20 m. If the length of the single-mode fiber 32 is shorter than 1 m, flat continuous white light may not be obtained in some cases. If the fiber length exceeds 20 m, generation efficiency of the entire spectrum is decreased, and beams in wavebands out of a measurement target are increased. Note that the length of the single-mode fiber 32 is preferably 3 m to 10 m, which allows continuous white light in the measurement waveband to be generated stably and efficiently.

Furthermore, it is desirable to select a cutoff wavelength of the single-mode fiber 32 approximately equal to the wavelength of the excitation pulse beam 4. If the cutoff wavelength is shorter than the wavelength of the excitation pulse beam 4, input efficiency of coupling to the fiber is decreased, thereby possibly decreasing generation efficiency and bandwidth of the Stokes beam 5. If the cutoff wavelength is longer than the wavelength of the excitation pulse beam 4, the beam mode of the Stokes beam 5 is not TEM00 but is mixed with a higher-order mode, thereby preventing a single Gaussian beam from being obtained. Note that examples of the single-mode fiber 32 usable in the non-linear Raman spectroscopy apparatus 1 of the present embodiment include 460 HP and 630 HP manufactured by Nufern.

Still further, it is desirable to use the polarization-maintained single-mode fiber having the characteristics described above as the single-mode fiber 32. With this, the Stokes beam 5 linearly-polarized can be obtained, which has a plane of polarization that can normally match with that of the pump beam 3 for use as a linearly-polarized beam, thereby allowing a CARS signal to be approximately doubled. Note that examples of the polarization-maintained single-mode fiber usable in the non-linear Raman spectroscopy apparatus 1 of the present embodiment include PM-460-HP, PM-630-HP manufactured by Nufern and HB8600 manufactured by Fibercore Ltd.

Note that when the excitation pulse beam 4 is introduced to the single-mode fiber 32, it is desirable to use an objective lens having a numerical aperture NA in a range of 0.1 to 0.25 in order to make a coefficient of aperture match with a light-receiving NA of the fiber. On the other hand, on an emission side of the single-mode fiber 32, it is desirable to use an objective lens having a numerical aperture NA of 0.2 to 0.6 in order to make the beam diameter of the Stokes beam 5 match with the beam diameter of the pump beam 3.

When the polarization-maintained single-mode fiber is used as the single-mode fiber 32, a half-wave plate 31 is used in order to make the direction of the plane of polarization of the excitation pulse beam 4 match with an optical axis (a fast axis or a slow axis) of the polarization-maintained single-mode fiber. Note that when a normal single-mode fiber is used, the half-wave plate 31 is omitted.

Also, in this Stokes-beam generating unit 30, a long-pass filter 33 is placed on an emission side of the single-mode fiber 32. The long-pass filter 33 reflects a beam of white light generated in the single-mode fiber 32 on a short-wavelength side and passes only a beam on a long-wavelength side. With this, unwanted beams of wavebands can be eliminated from the generated Stokes beam 5. High-performance long-pass filters having a selection ratio with an optical density of 6 to 7 are commercially available. For example, in the non-linear Raman spectroscopy apparatus 1 of the present embodiment, LP03-532RU-25 manufactured by Semrock, Inc. can be used.

Furthermore, in the Stokes-beam generating unit 30, a mirror 34 for introducing the beam to the beam radiating unit 40 may be placed in place of an optical path of the Stokes beam 5.

Beam Radiating Unit 40

The beam radiating unit 40 radiates the test sample 2 with the pump beam 3 emitted from the pump-cum-probe-beam generating unit 20 and the Stokes beam 5 emitted from the Stokes-beam generating unit 30 coaxially superposed each other. The structure of this beam radiating unit 40 is not particularly restrictive, but can be configured of, for example, a notch filter 41, beam expanders 42 and 43, a mirror 44, an objective lens 45, and others.

Here, the beam expanders 42 and 43 are to make the beam diameter match with the entrance pupil diameter of the objective lens 45. For example, when the beam diameter is approximately 2 mm, the beam is let pass through three-fold beam expanders so as to have a beam diameter of approximately 6 mm at the time of entrance to the objective lens 45. Also, as the notch filter 41, NF-532U-25 manufactured by Semrock, Inc. can be used, for example.

Measuring Unit 50

The measuring unit 50 measures a CARS beam emitted from the test sample 2, and is provided with, for example, an objective lens 51, a short-pass filter 52, a spectroscope 53, and others. The short-pass filter 52 intercepts the pump beam 3 and the Stokes beam 5 and lets only the CARS beam pass through. Simultaneously, since fluorescence occurring at the test sample has a wavelength longer than the wavelength of the pump beam 3, fluorescence can be efficiently intercepted similarly to the pump beam 3 and the Stokes beam 5.

High-performance short-pass filters having a selection ratio with an optical density of 6 to 7 are commercially available. For example, in the non-linear Raman spectroscopy apparatus 1 of the present embodiment, SP01-532RU-25 manufactured by Semrock, Inc. can be used.

As the spectroscope 53, for example, a polychromator, monochromator, or PMT (photomultiplier tube) having mounted thereon a CCD (charge coupled device image sensor) or CMOS (complementary metal oxide semiconductor) array detector including a cooling function for reducing thermal noise can be used. As a polychromator, for example, Shamrock SR-303i manufactured by Andor Technology plc., can be used. In this case, 1200 diffraction gratings per millimeter are used. Also, as a CCD detector, Newton DU970N BV manufactured by Andor Technology plc. can be used.

Here, since the CARS beam is a feeble beam, it is desirable to suppress losses as much as possible. Also, the measuring unit 50 is desirably configured to be sufficiently shield from external surrounding light. Furthermore, the CARS beam may be introduced to an incident slit of the spectroscope 53 by using a lens system. Alternatively, as shown in FIG. 1, the CARS beam can be introduced by using a multimode optical fiber 54.

Operation of the Non-Linear Raman Spectroscopy Apparatus 1

Next, the operation of the non-linear Raman spectroscopy apparatus 1 of the present embodiment, that is, a method of measuring a CARS spectrum of the test sample 2 by using the non-linear Raman spectroscopy apparatus 1, is described. In the non-linear Raman spectroscopy apparatus 1 of the present embodiment, first at the light source unit 10, a pulse beam emitted from the laser 11 is divided by a polarization beam splitter 13 into two, which are then introduced to the pump-cum-probe-beam generating unit 20 and the Stokes-beam generating unit 30.

Here, the pulse beam emitted from the laser 11 may be divided by the polarization beam splitter 13 after the plane of polarization of the pulse beam is rotated by the half-wave plate 12. With this, the distribution ratio is adjusted.

Figure 2:
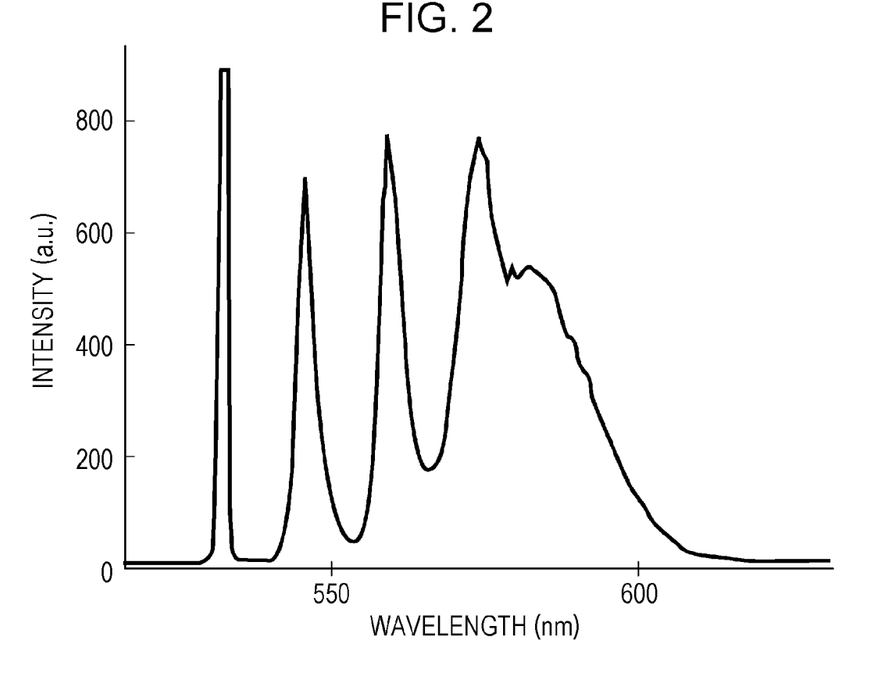
FIG. 2 is a graph showing a spectrum of a Stokes beam generated by using a single-mode fiber having a length of 6 m, with the horizontal axis representing wavelength and the vertical axis representing intensity.

Then, the pulse beam 4 entering the Stokes-beam generating unit 30 enters the single-mode fiber 32, where the pulse beam 4 is converted to the Stokes beam 5, which is continuous white light. FIG. 2 is a graph showing a spectrum of a Stokes beam generated by using a single-mode fiber having a length of 6 m, with the horizontal axis representing wavelength and the vertical axis representing intensity. Note that the spectrum shown in FIG. 2 is a spectrum of white continuous light generated from the pulse beam 4 having a wavelength of 532 nm and an incident power of 40 mW.

Here, when a polarization-maintained single-mode fiber is used as the single-mode fiber 32, the pulse beam 4 introduced from the light source unit 10 is let enter the single-mode fiber 32 via the half-wave plate 31. Specifically, the plane of polarization of the pulse beam 4 is rotated by the half-wave plate 31 so that the plane of polarization is parallel to a fast axis or a slow axis of the single-mode fiber 32. With this, polarization maintenance in the polarization-maintained single-mode fiber is ensured.

Figure 3:
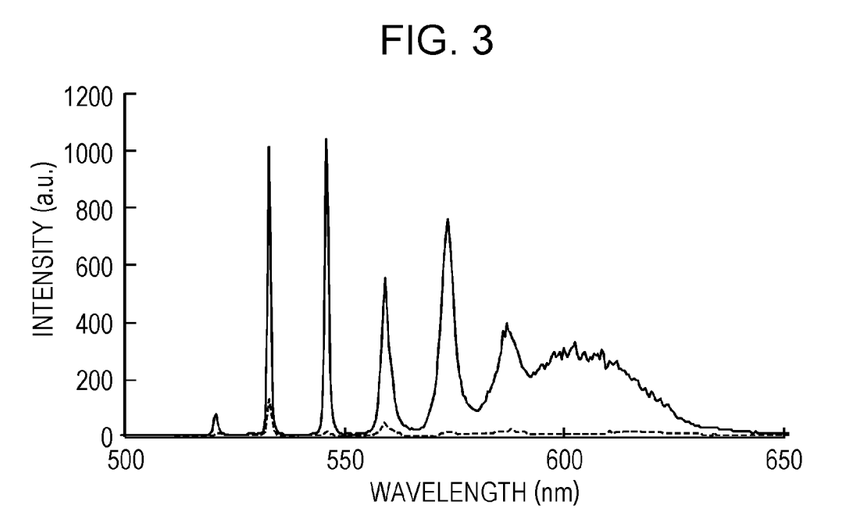
FIG. 3 is a graph showing a wavelength distribution of emitted light from a single-mode fiber when a plane of polarization of an incident excitation beam is matched with a fast axis or a slow axis of a polarization-maintained single-mode fiber, with the horizontal axis representing wavelength and the vertical axis representing intensity.

FIG. 3 is a graph showing a wavelength distribution of emitted light from a single-mode fiber when a plane of polarization of an incident excitation beam is matched with a fast axis or a slow axis of a polarization-maintained single-mode fiber, with the horizontal axis representing wavelength and the vertical axis representing intensity. As shown in FIG. 3, when the orientation of an analyzer is matched with the fast axis or the slow axis to measure a spectrum intensity distribution of the emitted beam, any one of approximately all wavelengths can be extinguished, and the Stokes beam 5 having a single linear polarization characteristic can be generated. Note that regarding distribution lines shown in FIG. 3, which represents the fast axis or the slow axis is not specified.

Also, before being introduced to the beam radiating unit 40, the Stokes beam 5 emitted from the single-mode fiber 32 is let pass through the long-pass filter 33 to remove components on a short-wavelength side. Specifically, for example, when the excitation pulse beam 4 is 532 nm, components having a wavelength shorter than 540 nm are removed so as to include this excitation pulse beam 4. With this, unwanted short-wavelength components included in the beam emitted from the single-mode fiber 32 are intercepted, and a signal-to-noise (background) ratio of the CARS spectrum to be measured can be improved.

On the other hand, the pulse beam (the pump beam 3) entering the pump-cum-probe-beam generating unit 20 has its optical path length adjusted by the plurality of mirrors 22a to 22d, 23a, 23b, 24, 25a, and 25b so that the pulse beam is introduced to the beam radiating unit 40 simultaneously with the Stokes beam 5. Here, with the use of the half-wave plate 21, the direction of the plane of polarization of the pump beam 3 is matched with the direction of the plane of polarization of the Stokes beam 5. With this, third-order non-linear optical process can be used in a highly efficient manner, thereby improving a signal-to-noise (background) ratio of the CARS spectrum.

Figure 4:
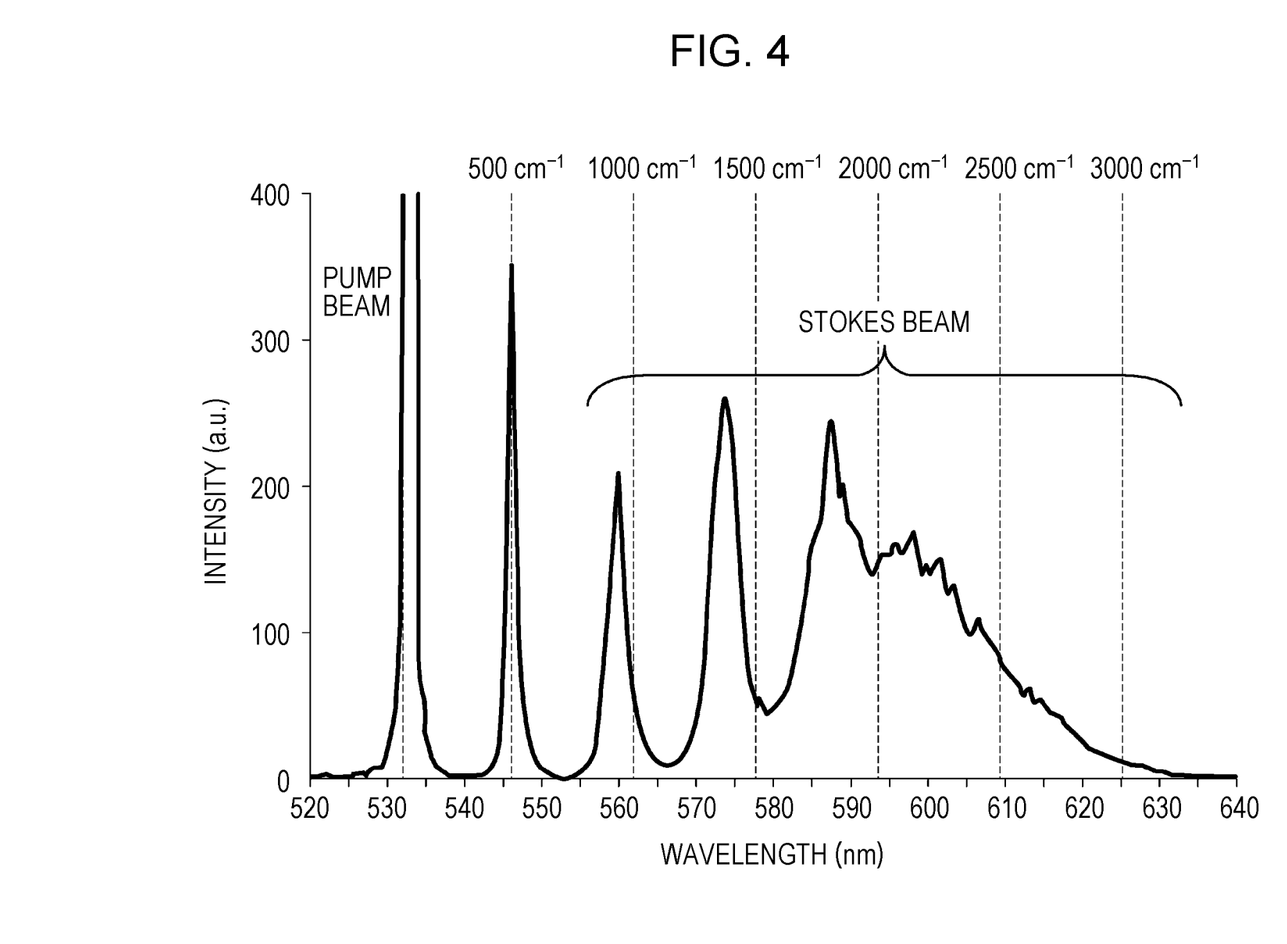
FIG. 4 is a graph showing spectrums of a Stokes beam generated by using a single-mode fiber having a length of 6 m and a pump beam, with the horizontal axis representing wavelength and the vertical axis representing intensity.

Regarding the pump beam 3 and the Stokes beam 5 introduced to the beam radiating unit 40, the pump beam 3 is reflected from the notch filter 41, and the Stokes beam 5 passes therethrough. Note that a long-pass filter can be used in place of the notch filter 41. Then, after the pump beam 3 and the Stokes beam 5 have their beam diameters enlarged at the beam expanders 42 and 43 so as to match with the entrance pupil diameter of the objective lens 45, the test sample 2 is radiated with these beams via the objective lens 45. FIG. 4 is a graph showing spectrums of a Stokes beam generated by using a single-mode fiber having a length of 6 m and a pump beam, with the horizontal axis representing wavelength and the vertical axis representing intensity.

Then, in the measuring unit 50, a CARS beam emitted from the test sample 2 is detected to obtain a Raman spectrum. Specifically, the CARS beam emitted from the test sample 2 is gathered by the objective lens 51, and is then detected by the spectroscope 53 with unwanted beams, such as the pump beam 3 and the Stokes beam 5, being intercepted by the short-pass filter 52.

Figure 5:
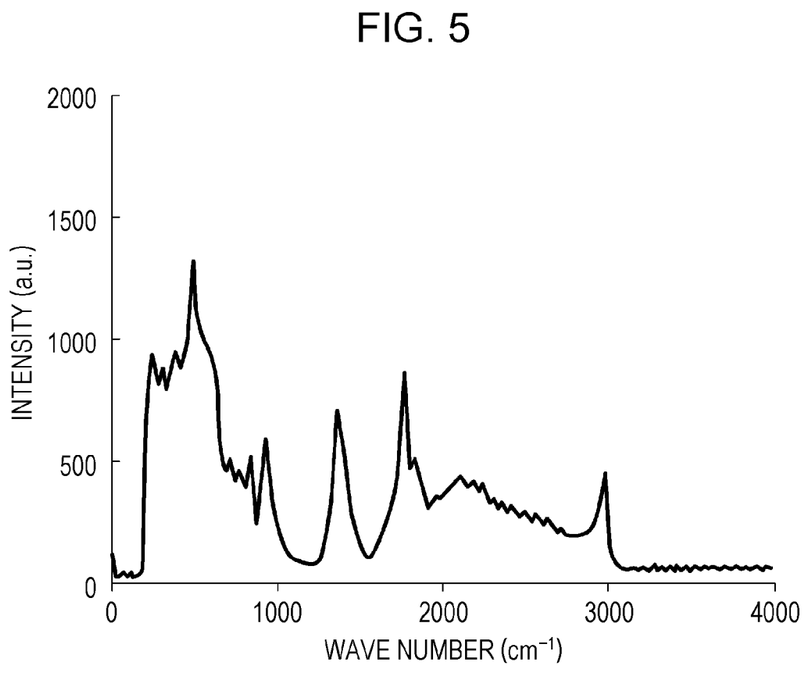
FIG. 5 is a graph of a CARS spectrum of a polymethylmethacrylate plate having a thickness of 2 mm, with the horizontal axis representing wavelength and the vertical axis representing intensity.

FIG. 5 is a graph of a CARS spectrum of a polymethylmethacrylate plate having a thickness of 2 mm, with the horizontal axis representing wavelength and the vertical axis representing intensity. Note that the spectrum shown in FIG. 5 was measured by using the objective lens 45 having an NA of 0.45 and the objective lens 51 having an NA of 0.3, with a wavelength of the laser 11 being 532 nm, a repetition rate of 30 kHz, and a pulse width of approximately 600 ps. Also, an incident average power of the pump beam 3 emitted from the objective lens 45 was 4 mW, an average power of the Stokes beam 5 was 6 mW, and an exposure time of the CCD detector was 500 ms.

As shown in FIG. 5, according to the non-linear Raman spectroscopy apparatus 1 of the present embodiment, an excellent CARS spectroscopic spectrum was obtained in a wide range covering a molecular fingerprint region of 500 $cm^{-1}$ to 3000 $cm^{-1}$. In the non-linear Raman spectroscopy apparatus 1 of the present embodiment, an operation of adjusting a time delay or the like can be eliminated, and spectrums in this band can be collectively obtained.

As has been described above in detail, in the non-linear Raman spectroscopy apparatus 1 of the present embodiment, the Stokes beam 5 is generated with the use of the single-mode fiber 32. Therefore, the structure can be simplified, and the size and cost of the apparatus can be decreased. Also, as for the single-mode fiber 32, its output is a Gaussian beam, and its incident end face is less damaged. Thus, the highly-stable Stokes beam 5 can be obtained with a simple coupling method and alignment.

Note that while an example of using a normal SMF as a continuous white light source in cascade stimulated Raman scattering has been suggested in the past, its application to non-linear Raman spectroscopy has not yet been reported. The reason for this can be thought that a plurality of peaks appear in SMF cascade stimulated Raman scattering.

Also, in the non-linear spectroscopy measurement system described in Japanese Unexamined Patent Application Publication No. 2009-222531, although a polarization state of supercontinuum light (beam) is not particularly described, in order to effectively use a coherent third-order non-linear optical process, it is important to establish linear polarization with matched polarization of the pump beam, the probe beam, and the Stokes beam (a broadband beam). In the non-linear Raman spectroscopy apparatus 1 of the present embodiment, the direction of the plane of the polarization of the pump beam 3 is matched with the direction of the plane of polarization of the Stokes beam 5. Therefore, the third-order non-linear optical process can be efficiently used.

In particular, an apparatus using a polarization-maintained single-mode fiber can easily perform beam adjustment of the pump beam and the Stokes beam (alignment in which the beam diameters are made equal to each other and directions are made the same), and therefore is suitable for microspectroscopy and imaging.

2. Another Embodiment
Entire Structure of the Apparatus

Figure 6:
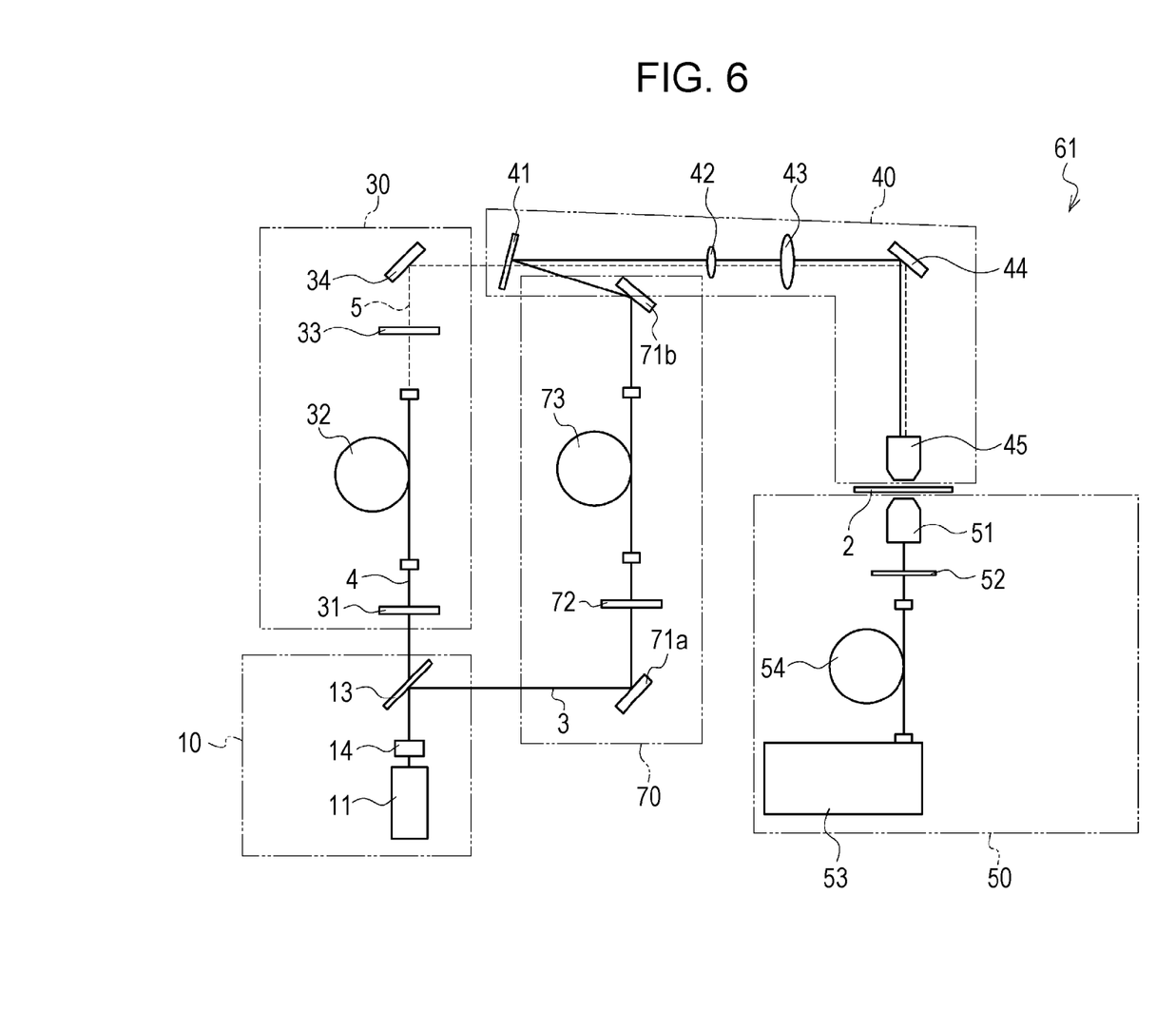
FIG. 6 is a schematic diagram of the structure of a non-linear Raman spectroscopy apparatus according to another embodiment of the present disclosure.

Next, a non-linear Raman spectroscopy apparatus according to another embodiment of the present disclosure is described. FIG. 6 is a schematic diagram of the structure of the non-linear Raman spectroscopy apparatus according to the present embodiment. Note that structures identical to those of the non-linear Raman spectroscopy apparatus 1 of the embodiment described first shown in FIG. 1 are provided with the same reference numeral and are not described in detail herein.

As shown in FIG. 6, in a non-linear Raman spectroscopy apparatus 61 of the present embodiment, the pump-cum-probe-beam generating unit 70 has an optical-path-length adjusting mechanism configured not to have a beam reflected by a mirror but to let a beam pass through an optical fiber 73 having a predetermined length. Specifically, a pulse beam introduced from the light source unit 10 enters the optical fiber 73 with an optical path of the beam being changed by a mirror 71a. Then, with the beam passing though the optical fiber 73, its optical path length is adjusted, and then the optical path is changed by a mirror 71b and the beam is emitted to the beam radiating unit 40.

Pump-Cum-Probe-Beam Generating Unit 70

As the optical fiber 73 placed in the pump-cum-probe-beam generating unit 70, a single-mode fiber or a polarization-maintained single-mode fiber can be used when a low excitation power equal to or lower than several mW is inputted. This is because, when the excitation power is low, stimulated Raman scattering light does not occur in a cascade manner in the fiber and the fiber can be used simple for optical transmission. An example of the single-mode fiber usable in this case is 630HP manufactured by Nufern. Examples of the polarization-maintained fiber include PM-460-HP manufactured by Nufern and HB8600 manufactured by Fibercore Ltd.

On the other hand, when the excitation power is gradually increased, stimulated Raman scattering light occurs, thereby preventing a single-wavelength pump-probe pulse from being sent. According to an experiment of the inventor, a threshold of the excitation input power capable of preventing stimulated Raman scattering was up to approximately 5 mW. Therefore, when an excitation power equal to or larger than several mW is inputted, the fiber diameter is increased as appropriate, and it is desirable to use, for example, a polarization-maintained single-mode fiber having a fiber core diameter equal to or larger than 8 μm, a multi-mode fiber having a core diameter equal to or smaller than 100 μm, or a so-called large-mode-area fiber or photonic crystal large-mode-area fiber.

Here, in the case of a single-mode fiber, for example, SMF-28-J9 manufactured by Nufern can be used. In the case of a polarization-maintained single-mode fiber, for example, PM1550-HP manufactured by Nufern can be used. In the case of a large-mode-area fiber, for example, P-10/125DC, or P-25/240DC, P-40/140DC manufactured by Thorlabs can be used. In the case of a large-mode-area photonic crystal fiber, for example, LMA-20 manufactured by NKT Photonics A/S can be used. In the case of an endless single-mode photonic crystal fiber, for example, ESM-12-01 manufactured by NKT Photonics A/S can be used.

Here, when a polarization-maintained single-mode fiber is used as the single-mode fiber 32, a half-wave plate 72 is placed before the optical fiber 73 to match direction of the plane of polarization of the pump beam 3 with the direction of the plane of polarization of the Stokes beam 5. Note that when a normal single-mode fiber is used, the half-wave plate 72 can be eliminated.

Light Source Unit 10

In the non-linear Raman spectroscopy apparatus 61 of the present embodiment, a second harmonic generation optical crystal 14 is placed in the light source unit 10. With this second harmonic generation optical crystal 14, an excitation beam emitted from the laser 11 is wavelength-converted to a pump beam. Specifically, for example, when the excitation beam is 1064 nm, green light of 532 nm is obtained by wavelength conversion.

In the non-linear Raman spectroscopy apparatus 61 of the present embodiment, the optical path length of the pump beam 3 is adjusted by using the optical fiber 73. Therefore, it is easy to adjust the timing with the Stokes beam 5, and the apparatus can be made small in size. In CARS spectroscopy, the pump beam 3 and the Stokes beam 5 are to reach at a measurement point on the test sample simultaneously. By using the optical fiber 73, it is easy to make the optical path length of the pump beam 3 and the optical path length of the Stokes beam 5 equal to each other.

Note that the structures and effects other than those described above in the present embodiment are similar to those of the embodiment described first.

3. Still Another Embodiment
Entire Structure of the System

Figure 7:
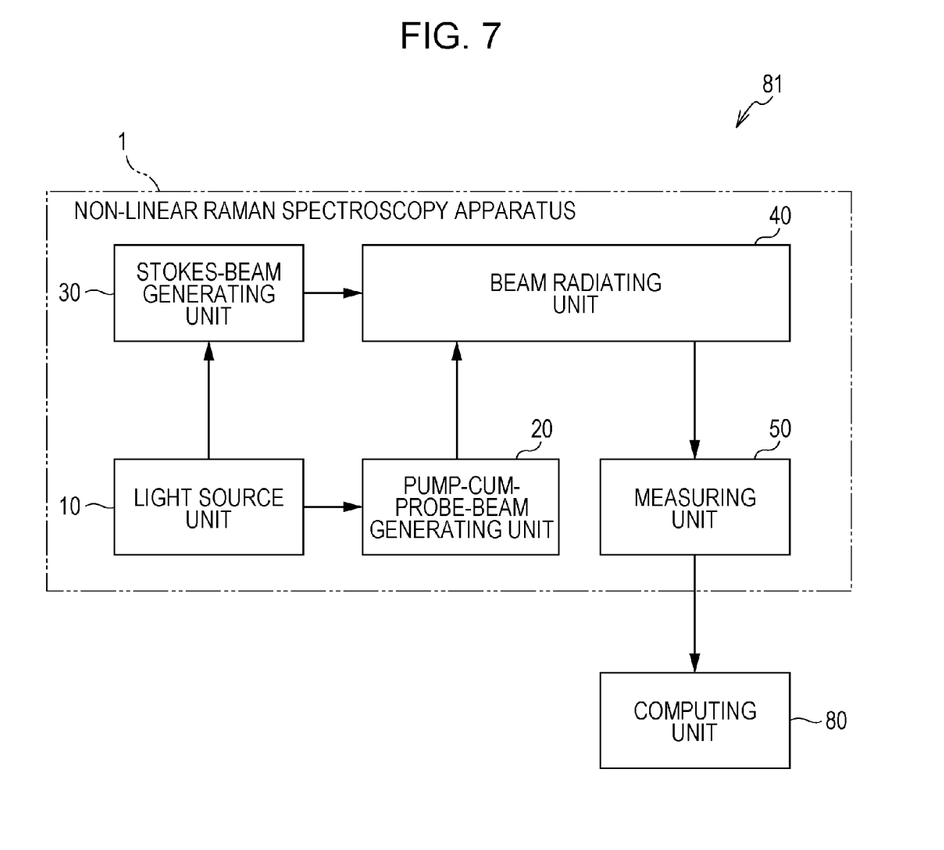
FIG. 7 is a conceptual diagram of the structure of a non-linear Raman spectroscopy system according to still another embodiment of the present disclosure.

Next, a non-linear Raman spectroscopy system according to still another embodiment of the present disclosure is described. FIG. 7 is a conceptual diagram of the structure of the non-linear Raman spectroscopy system according to the present embodiment. Note that structures identical to those of the non-linear Raman spectroscopy apparatus 1 of the embodiment described first shown in FIG. 1 are provided with the same reference numeral and are not described in detail herein.

As shown in FIG. 7, a non-linear Raman spectroscopy system 81 is a system including the non-linear Raman spectroscopy apparatus 1 according to the embodiment described first, and a computing unit 80 is connected to the measuring unit 50 of the non-linear Raman spectroscopy apparatus 1.

Computing Unit 80

In computing unit 80, an electronic calculator as a computing device, a display device, and others are provided. Distribution of CARS spectrums detected by the spectroscope of the measuring unit 50 is normalized, and its results and others are displayed. A specific computing method for normalization is described below.

A multiplex CARS spectrum includes a degenerated four-wave mixing (2-color CARS) component and a non-degenerated four-wave mixing (3-color CARS) component (refer to Young Jong Lee and Marcus T. Cicerone: "Single-shot interferometric approach to background free broadband coherent anti-Stokes Raman scattering spectroscopy", 5 Jan. 2009/Vol. 17, No. 1/OPTICS EXPRESS 123).

Here, in CARS spectroscopy, the degenerated four-wave mixing (2-color CARS) component has the same pump beam and probe beams and Stokes beam different therefrom and, in general, is often referred to as a CARS spectrum in a narrow sense. On the other hand, in multiplex CARS, the non-degenerated four-wave mixing (3-color CARS) component with all of the pump beam, the probe beam, and the Stokes beam having different wavelengths may become anti-Stokes Raman scattering light having the same degenerated four-wave mixing (2-color CARS) component.

On the other hand, in the non-linear Raman spectroscopy apparatus 1 used in the non-linear Raman spectroscopy system 81 of the present embodiment, compared with a Stokes beam (continuous white light), the pump beam and the probe beam can be regarded as line spectrums in a sufficiently narrow band. Therefore, a degenerated four-wave mixing (2-color CARS) component $I_{2-color}(\omega)$ is proportional to the product of the square of a power $P_P$ of the pump beam and a Stokes-beam intensity distribution $S_S(\omega)$, and is represented by Expression 7 below, where $\omega$ in Expression 7 below represents a wave number (cm$^{-1}$).

$$I_{2-color}(\omega) \propto \left(\frac{P_P}{2}\right)^2 S_S(\omega) \qquad \text{Expression 7}$$

Also, as for a non-degenerated four-wave mixing (3-color CARS) component $I_{3-color}(\omega)$, two wavelength components (wave number components) in a spectrum of a continuous broadband beam serve as a pump beam and a Stokes beam. Therefore, the CARS spectrum can be approximately considered as being proportional to the product of an autocorrelation function of the Stokes-beam intensity distribution regarding wave numbers $\omega$ and $\omega'$ and a pump-beam power, and is represented by Expression 8 below.

$$I_{3-color}(\omega) \propto P_P \int S_S(\omega')S_S(\omega+\omega')d\omega' \qquad \text{Expression 8}$$

A sum of Expression 7 and Expression 8 above is represented by Expression 9 below.

$$R_N(\omega) = I_{2-color} + I_{3-color} \qquad \text{Expression 9}$$

-continued $$= \left(\frac{P_P}{2}\right)^2 S_S(\omega) + P_P \int S_S(\omega')S_S(\omega+\omega')d\omega'$$

When $R_N(\omega)$ found from Expression 9 above is taken as a normalization factor to normalize a CARS measurement spectrum $S_C(\omega)$, a normalized CARS spectrum $S_N(\omega)$ is given by Expression 10 below.

$$S_N(\omega) = \frac{S_C(\omega)}{R_N(\omega)} \qquad \text{Expression 10}$$

Figure 8:
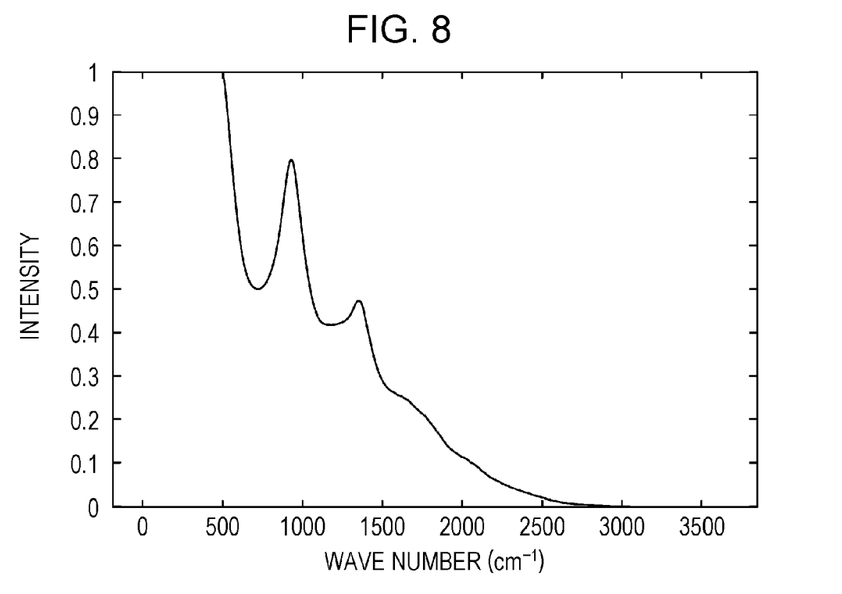
FIG. 8 is a graph showing an autocorrelation function of a Stokes-beam intensity distribution, with the horizontal axis representing wavelength and the vertical axis representing intensity.
Figure 9:
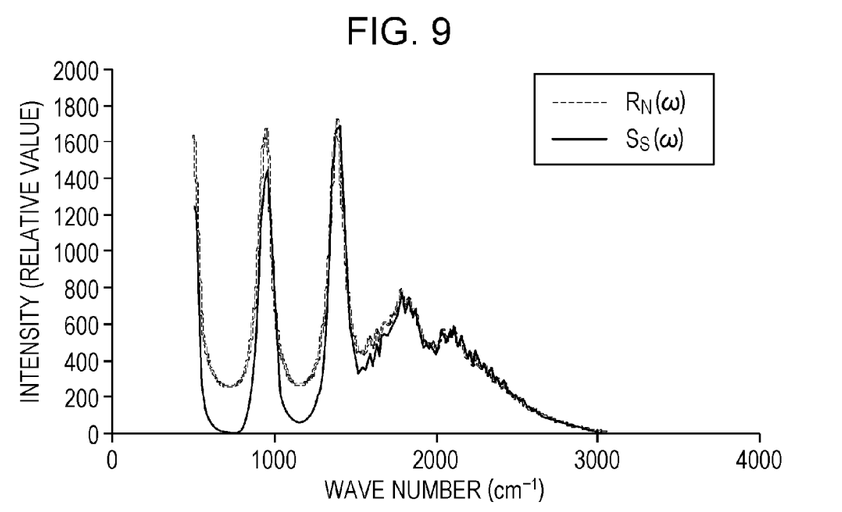
FIG. 9 is a graph showing a Stokes-beam intensity distribution, with the horizontal axis representing wavelength and the vertical axis representing intensity.

FIG. 8 is a graph showing an autocorrelation function of a Stokes-beam intensity distribution, with the horizontal axis representing wavelength and the vertical axis representing intensity. FIG. 9 is a graph showing a Stokes-beam intensity distribution, with the horizontal axis representing wavelength and the vertical axis representing intensity. Note that a normalization factor $R_N(\omega)$ in Expression 9 is also shown. Furthermore, FIG. 10 is a diagram showing the results obtained by normalizing a CARS spectrum of a polyethylene-terephthalate plate having a thickness of 1 mm based on Expression 10 above.

Figure 10:
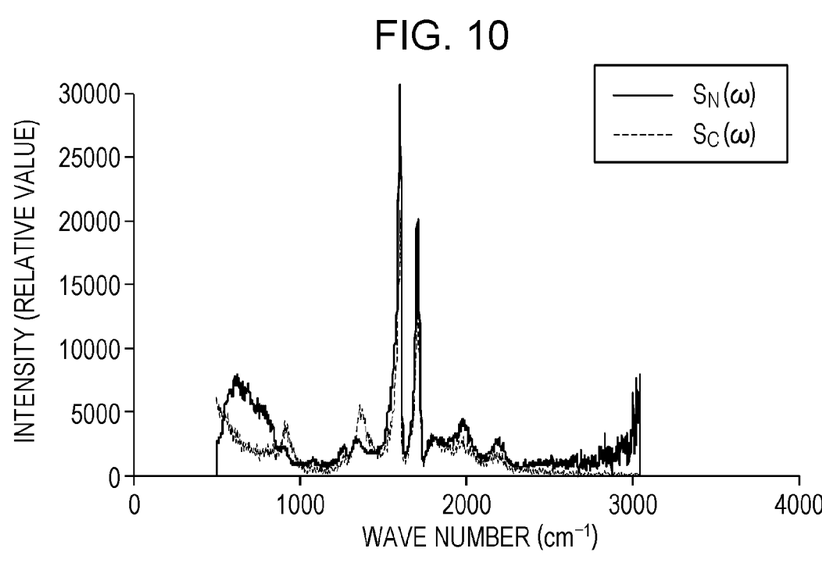
FIG. 10 is a diagram showing the results obtained by normalizing a CARS spectrum of a polyethylene-terephthalate plate having a thickness of 1 mm based on Expression 10.

As shown in FIG. 8 to FIG. 10, it has been confirmed that, with normalization by using the method of the present embodiment, a pseudo-peak appearing from 500 cm$^{-1}$ to 1000 cm$^{-1}$ disappears to mitigate spectrum noise. Note that the spectrums depicted in FIG. 8 to FIG. 10 were measured on the condition that an incident average power of the pump beam 3 emitted from the objective lens 45 was 4 mW, an average power of the Stokes beam 5 was 3 mW, and an exposure time of the CCD detector was 300 ms.

In this manner, with normalization in the computing unit 80, even if a non-flat Stokes-beam intensity distribution is present, a correct CARS spectrum intensity distribution can be obtained without confusing a pseudo-spectrum peak of the CARS spectrum to be measured not corresponding to molecular vibration with a correct one.

Also, in the Stokes-beam intensity distribution obtained from the non-linear Raman spectroscopy system 81 of the present embodiment, the occurrence of continuous white light is based on cascade stimulated Raman scattering in the single-mode fiber. Therefore, on a low wave range (on a short-wavelength side), a peak occurs in approximately every 440 cm$^{-1}$, which is a Raman shift due to a silica core (SiO$_2$) in the single-mode fiber, and thus the spectrum is not flat.

In general, the edge wavelength of a long-pass filter for removing an unwanted component of a beam emitted from a single-mode fiber where a Stokes beam occurs is set to be a wavelength slightly longer than that of the pump beam. With this, the wavelength is shifted to a long-wavelength side up to a wavelength with which the spectrum relatively becomes flat. In that case, degenerated four-wave mixing (2-color CARS) components on a low wave number side are reduced or removed, but non-degenerated four-wave mixing (3-color CARS) components remain. This is because in the non-degenerated four-wave mixing (3-color CARS) components, a wave number representing a difference between two optical components in the Stokes-beam intensity distribution includes a low wave number component.

Thus, an edge wavelength of the long-pass filter provided after emission from the Stokes-beam-generation single-mode fiber is set. With this, by using only a portion having a relatively flat Stokes-beam intensity distribution characteristic, an excellent CARS spectrum can be obtained without impairing the measurement wave-number region. A setting condition of setting the edge wavelength of the long-pass filter can be given as follows.

Figure 11:
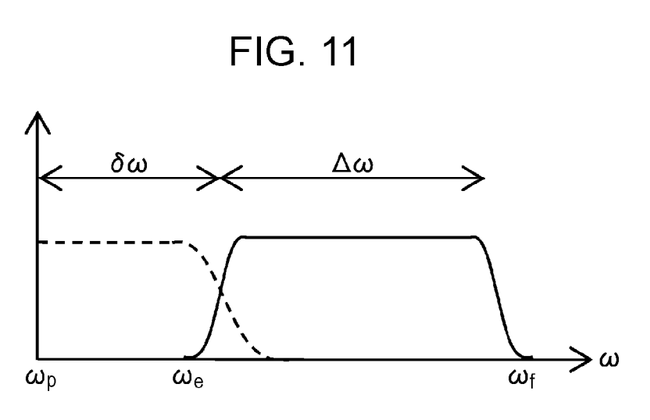
FIG. 11 is a diagram showing a method of deriving a conditional expression represented by Expression 11.

For example, when the edge wavelength on a short-wavelength side of the long-pass filter is $\lambda_e$(nm), the wavelength of the pump beam is $\lambda_p$(nm), and the measurement maximum wave number is $\omega_m$(cm$^{-1}$), the condition of $\lambda_e$(nm) is represented by Expression 11 below. Note that $\lambda_f$ in Expression 11 below is a value found from Equation 12 below, and the relation between the wave number $\omega$ (cm$^{-1}$) and the wavelength $\lambda$ (nm) is represented by Equation 6 above. FIG. 11 is a method of deriving a conditional expression represented by Expression 11 above.

$$\lambda_p \le \lambda_e \le \frac{2\lambda_p\lambda_f}{\lambda_p + \lambda_f} \quad \text{Expression 11}$$

$$\lambda_f = \frac{1 \times 10^7 \cdot \lambda_p}{1 \times 10^7 - \omega_m \cdot \lambda_p} \quad \text{Expression 12}$$

In the case of a band-pass filter, the band-pass region can be $\lambda_e < \lambda < \lambda_f$. Here, regarding the CARS spectrum shown in FIG. 8 to FIG. 10, edge wavelength settings of the long-pass filter are made by using the method described above. For example, if $\lambda_p$=532 nm and $\omega_m$=3000 cm$^{-1}$, then $\lambda_f$=633 nm holds from Expression 12 above. Therefore, it is found from Expression 11 above that $\lambda_e$ can be in a range of $\lambda_p$(=532 nm)<$\lambda_e$<578 nm.

Therefore, when $\lambda_e$=575 nm, from Expression 6 above, $\Delta\omega=\{(1\times10^7)/\lambda_e\}-\{(1\times10^7)/\lambda_f\}=1594$ cm$^{-1}$ and $\delta\omega=\{(1\times10^7)/\lambda_p\}-\{(1\times10^7)/\lambda_e\}=1406$ cm$^{-1}$ are obtained. And, as shown in FIG. 11, if $\Delta\omega$ and $\delta\omega$ satisfy the inequality shown in Expression 13 below, a CARS spectrum can be obtained in all wave number region (0 to $\omega_m$).

$$\delta\omega < \Delta\omega \quad \text{Expression 13}$$

Note that a long-pass filter having an edge wavelength of 575 nm manufactured by Edmund Optics was used. In this case, non-degenerated four-wave mixing (3-color CARS) components are in a range of 4 cm$^{-1}$ to 1406 cm$^{-1}$, and degenerated four-wave mixing (2-color CARS) components are in a range of 1406 cm$^{-1}$ to 3000 cm$^{-1}$.

In this manner, the non-flat Stokes-beam region is removed by using a long-pass filter or a band-pass filter. With this, in spite of using only the portion having a flat Stokes-beam intensity distribution, an excellent CARS spectrum can be easily obtained without impairing a measured wave number (wavelength) region.

Figure 12:
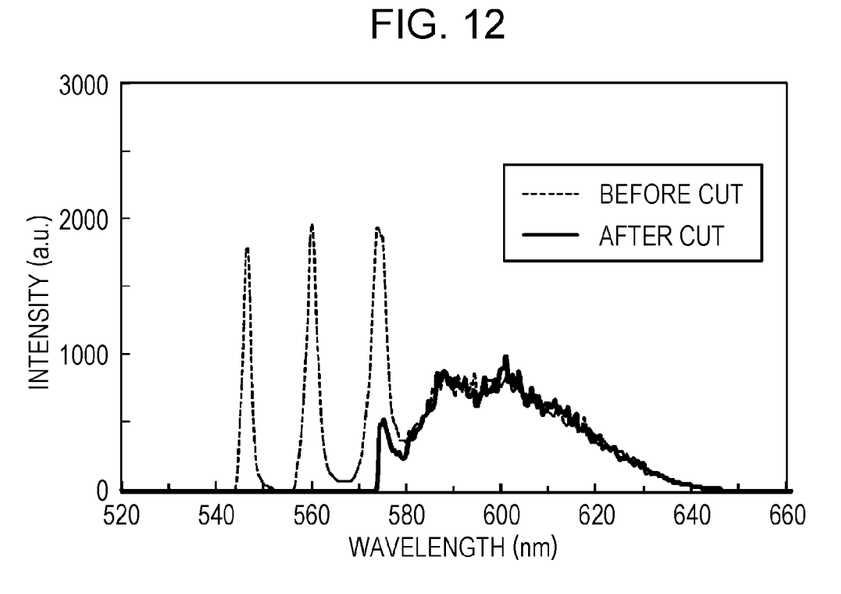
FIG. 12 is a graph showing an intensity distribution of a Stokes beam with its short-wavelength components being cut by an LPF, with the horizontal axis representing wavelength and the vertical axis representing intensity.
Figure 13:
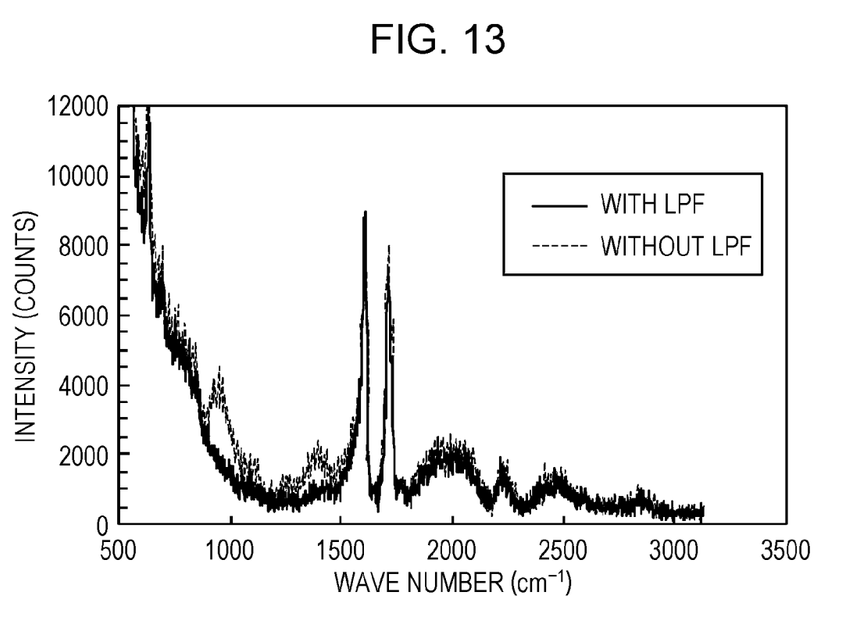
FIG. 13 is a graph showing a CARS spectrum of a polyethylene-terephthalate plate having a thickness of 1 mm measured based on the intensity distribution of the Stokes beam shown in FIG. 12.
Figure 14:
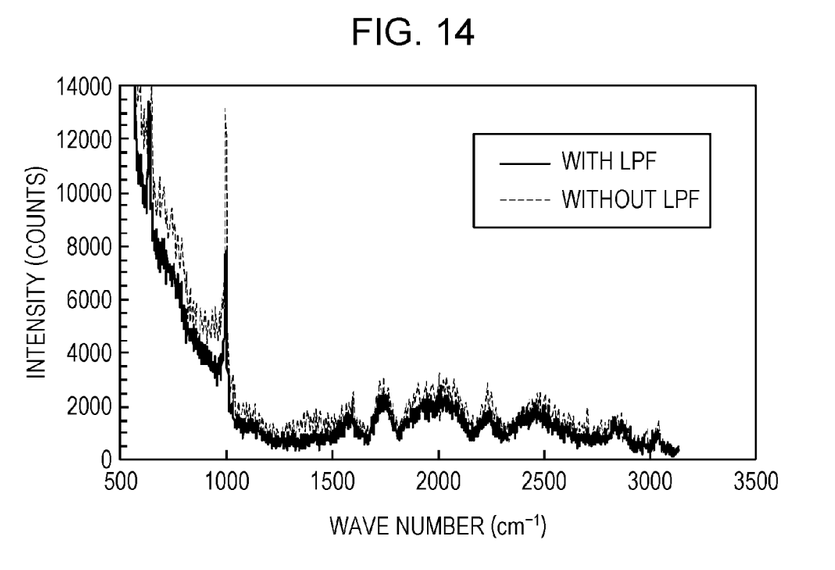
FIG. 14 is a graph showing a CARS spectrum of a polystyrene plate having a thickness of 1 mm measured based on the intensity distribution of the Stokes beam shown in FIG. 12.

FIG. 12 is a graph showing an intensity distribution of a Stokes beam with its short-wavelength components being cut by an LPF, with the horizontal axis representing wavelength and the vertical axis representing intensity. FIG. 13 is a graph showing a CARS spectrum of a polyethylene-terephthalate plate having a thickness of 1 mm measured based on the intensity distribution of the Stokes beam shown in FIG. 12. FIG. 14 is a graph showing a CARS spectrum of a polystyrene plate having a thickness of 1 mm.

As shown in FIG. 13, while a pseudo-spectrum peak were observed near 900 cm$^{-1}$ and near 1400 cm$^{-1}$ in the CARS spectrum of the polyethylene-terephthalate plate without using a long-pass filter, such pseudo spectrums did not occur in the CARS spectrum measured by using a long-pass filter, and excellent results were obtained.

Also, as shown in FIG. 14, similar effects can be confirmed also in the CARS spectrum of the polystyrene plate. Note that in the spectrum shown in FIG. 14, a spectrum peak near 1000 cm$^{-1}$ is due to non-degenerated four-wave mixing (3-color CARS).

The present disclosure can take the following structure.

(1) A non-linear Raman spectroscopy apparatus including
 a light source unit emitting a pulse beam having a pulse width of 0.2 ns to 10 ns, a pulse peak power of 50 W to 5000 W, and a wavelength of 500 nm to 1200 nm, and
 a single-mode fiber through which continuous white light is generated from the pulse beam, wherein
 a test sample to be measured is radiated with a pump-cum-probe beam formed of the pulse beam and a Stokes beam formed of the continuous white light to obtain a Raman spectrum.
(2) The non-linear Raman spectroscopy apparatus according to (1), wherein the single-mode fiber is a polarization-maintained single-mode fiber.
(3) The non-linear Raman spectroscopy apparatus according to (2), further including a half-wave plate rotating a plane of polarization of the pulse beam introduced from the light source unit, wherein the pulse beam having the plane of polarization rotated by the half-wave plate so as to be parallel to a fast axis or a slow axis of the single-mode fiber enters the single-mode fiber.
(4) The non-linear Raman spectroscopy apparatus according to (2) or (3), further including a half-wave plate matching a direction of a plane of polarization of the pump-cum-probe beam with a plane of polarization of the Stokes beam.
(5) The non-linear Raman spectroscopy apparatus according to any one of (1) to (4), wherein the single-mode fiber has a fiber length of 1 m to 20 m.
(6) The non-linear Raman spectroscopy apparatus according to any one of (1) to (5), further including an optical fiber through which an optical path length of the pump-cum-probe beam is adjusted so that the test sample is radiated with the pump-cum-probe beam and the Stokes beam simultaneously.
(7) The non-linear Raman spectroscopy apparatus according to (6), wherein the optical fiber is a polarization-maintained single-mode fiber having a fiber core diameter equal to or larger than 8 μm, a multimode fiber having a core diameter equal to or smaller than 100 μm, or a large-mode-area fiber or a photonic crystal large-mode-area fiber.
(8) A non-linear Raman spectroscopy system including
 the non-linear Raman spectroscopy apparatus according to any one of (1) to (7), and
 a computing device normalizing a Raman spectroscopic spectrum measured in the non-linear Raman spectroscopy apparatus.
(9) The non-linear Raman spectroscopy system according to (8), wherein, in the computing device, when $\omega$ and $\omega'$ each represent a wave number (cm$^{-1}$), a normalization factor $R_N(\omega)$ is calculated from a power $P_P$ of the pump beam and an intensity spectrum distribution $S_S(\omega)$ of the Stokes beam based on Expression 1 above, and a measurement spectrum $S_C(\omega)$ is normalized with the normalization factor $R_N(\omega)$ based on Expression 2 above to find a normalized spectrum $S_N(\omega)$.
(10) The non-linear Raman spectroscopy system according to (9), wherein a long-pass filter or a band-pass filter having an edge wavelength $\lambda_e$ (nm) on a short-wavelength side in a range represented by Expression 3 and Expression 4 above is provided on an emission side of the single-mode fiber when a wavelength of the pump beam is $\lambda_p$ (nm) and a measurement maximum wave number is $\omega_m$ (cm$^{-1}$).

(11) A non-linear Raman spectroscopy method including emitting a pulse beam from a light source unit, the pulse beam having a pulse width of 0.2 ns to 10 ns, a pulse peak power of 50 W to 5000 W, and a wavelength of 500 nm to 1200 nm, generating continuous white light from the pulse beam through a single-mode fiber, and radiating a test sample to be measured with a pump-cum-probe beam formed of the pulse beam and a Stokes beam formed of the continuous white light to obtain a Raman spectrum.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A non-linear Raman spectroscopy apparatus comprising:
   a light source unit emitting a pulse beam having a pulse width of 0.2 ns to 10 ns, a pulse peak power of 50 W to 5000 W, and a wavelength of 500 nm to 1200 nm; and
   a single-mode fiber through which continuous white light is generated from the pulse beam; wherein the single-mode fiber is a polarization-maintained single-mode fiber; and
   wherein a test sample to be measured is radiated with a pump-cum-probe beam formed of the pulse beam and a Stokes beam formed of the continuous white light to obtain a Raman spectrum.

2. The non-linear Raman spectroscopy apparatus according to claim 1, wherein the single-mode fiber has a fiber length of 1 m to 20 m.

3. The non-linear Raman spectroscopy apparatus according to claim 2, further comprising:
   a half-wave plate rotating a plane of polarization of the pulse beam introduced from the light source unit; wherein
   the pulse beam having the plane of polarization rotated by the half-wave plate so as to be parallel to a fast axis or a slow axis of the single-mode fiber enters the single-mode fiber.

4. The non-linear Raman spectroscopy apparatus according to claim 2, further comprising a half-wave plate matching a direction of a plane of polarization of the pump-cum-probe beam with a plane of polarization of the Stokes beam.

5. The non-linear Raman spectroscopy apparatus according to claim 1, wherein the single-mode fiber has a fiber length of 1 m to 20 m.

6. The non-linear Raman spectroscopy apparatus according to claim 1, further comprising an optical fiber through which an optical path length of the pump-cum-probe beam is adjusted so that the test sample is radiated with the pump-cum-probe beam and the Stokes beam simultaneously.

7. The non-linear Raman spectroscopy apparatus according to claim 6, wherein the optical fiber is a polarization-maintained single-mode fiber having a fiber core diameter equal to or larger than 8 μm, a multimode fiber having a core diameter equal to or smaller than 100 μm, or a large-mode-area fiber or a photonic crystal large-mode-area fiber.

8. A non-linear Raman spectroscopy system comprising:
   the non-linear Raman spectroscopy apparatus according to claim 1; and
   a computing device normalizing a Raman spectroscopic spectrum measured in the non-linear Raman spectroscopy apparatus.

9. The non-linear Raman spectroscopy system according to claim 8, wherein, in the computing device, when $\omega$ and $\omega'$ each represent a wave number (cm$^{-1}$), a normalization factor $R_N(\omega)$ is calculated from a power $P_P$ of the pump beam and an intensity spectrum distribution $S_S(\omega)$ of the Stokes beam based on Expression (A) below, and a measurement spectrum $S_C(\omega)$ is normalized with the normalization factor $R_N(\omega)$ based on Expression (B) below to find a normalized spectrum $S_N(\omega)$ $$R_N(\omega) = \left(\frac{P_P}{2}\right)^2 S_S(\omega) + P_P \int S_S(\omega')S_S(\omega+\omega')d\omega' \quad (A)$$

$$S_N(\omega) = \frac{S_C(\omega)}{R_N(\omega)}. \quad (B)$$

10. The non-linear Raman spectroscopy system according to claim 9, wherein a long-pass filter or a band-pass filter having an edge wavelength $\lambda_e$ (nm) on a short-wavelength side in a range represented by Expression (C) below is provided on an emission side of the single-mode fiber when a wavelength of the pump beam is $\lambda_p$ (nm) and a measurement maximum wave number is $\omega_m$ (cm$^{-1}$)

$$\lambda_p \leq \lambda_e \leq \frac{2\lambda_p \lambda_f}{\lambda_p + \lambda_f} \quad (C)$$

Here, $$\lambda_f = \frac{1 \times 10^7 \cdot \lambda_p}{1 \times 10^7 - \omega_m \cdot \lambda_p}.$$

11. A non-linear Raman spectroscopy method comprising:
    emitting a pulse beam having a pulse width of 0.2 ns to 10 ns, a pulse peak power of 50 W to 5000 W, and a wavelength of 500 nm to 1200 nm from a light source unit;
    generating continuous white light from the pulse beam via a single-mode fiber; and
    radiating a test sample to be measured with a pump-cum-probe beam formed of the pulse beam and a Stokes beam formed of the continuous while light to obtain a Raman spectrum, wherein the continuous white light of the Stokes beam is generated with a polarization-maintained single-mode fiber.

* * * * *